United States Patent
Hong et al.

(10) Patent No.: US 9,091,668 B2
(45) Date of Patent: Jul. 28, 2015

(54) JOINT INSPECTION APPARATUS

(71) Applicant: KOH YOUNG TECHNOLOGY INC., Seoul (KR)

(72) Inventors: Deok-Hwa Hong, Gwangmyeong-si (KR); Joong-Ki Jeong, Seoul (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 121 days.

(21) Appl. No.: 13/852,133

(22) Filed: Mar. 28, 2013

(65) Prior Publication Data
US 2013/0259359 A1    Oct. 3, 2013

(30) Foreign Application Priority Data
Mar. 29, 2012 (KR) .................. 10-2012-0032152

(51) Int. Cl.
*G01N 21/956* (2006.01)
*G06T 7/00* (2006.01)
*G01B 11/24* (2006.01)

(52) U.S. Cl.
CPC .............. *G01N 21/956* (2013.01); *G01B 11/24* (2013.01); *G01N 21/95684* (2013.01); *G06T 7/0004* (2013.01); *G06T 7/0006* (2013.01); *G06T 7/0057* (2013.01); *G06T 2207/10152* (2013.01); *G06T 2207/30152* (2013.01)

(58) Field of Classification Search
USPC ................................................ 382/141–152
See application file for complete search history.

(56) References Cited

U.S. PATENT DOCUMENTS

| 4,454,585 | A  | * | 6/1984 | Ele ................................. | 382/150 |
| 5,064,291 | A  | * | 11/1991 | Reiser ........................... | 356/625 |
| 5,293,324 | A  | * | 3/1994 | Tokura .......................... | 382/141 |
| 5,448,359 | A  | * | 9/1995 | Schick et al. ................. | 356/609 |
| 5,455,870 | A  | * | 10/1995 | Sepai et al. ................... | 382/147 |
| 5,621,811 | A  | * | 4/1997 | Roder et al. .................. | 382/147 |
| 5,815,275 | A  | * | 9/1998 | Svetkoff et al. .............. | 356/608 |
| 6,023,663 | A  | * | 2/2000 | Kim ................................ | 702/81 |
| 6,853,744 | B2 | * | 2/2005 | Mueller et al. ................ | 382/147 |
| 6,862,365 | B1 | * | 3/2005 | Beaty et al. ................... | 382/145 |
| 7,085,411 | B2 | * | 8/2006 | Beaty et al. ................... | 382/154 |
| 7,231,013 | B2 | * | 6/2007 | Meyer ............................. | 378/58 |
| 7,525,669 | B1 | * | 4/2009 | Abdollahi ..................... | 356/603 |
| 7,610,168 | B2 | * | 10/2009 | Isumi et al. .................... | 702/179 |
| 7,822,261 | B2 | * | 10/2010 | Moriya et al. ................. | 382/147 |
| 8,125,632 | B2 | * | 2/2012 | Watanabe ...................... | 356/237.1 |
| 2001/0012107 | A1 | * | 8/2001 | Toh ................................. | 356/601 |

(Continued)

FOREIGN PATENT DOCUMENTS

KR    10-1059697    8/2011

*Primary Examiner* — Aaron W Carter
(74) *Attorney, Agent, or Firm* — Kile Park Reed & Houtteman PLLC

(57) ABSTRACT

Disclosed herein is a joint inspection apparatus for judging whether an electronic component mounted on a board is appropriately soldered to the board capable of increasing accuracy in judging a state of a joint by combining at least two joint features with each other and capable of allowing a user to intuitively and easily change a reference for judging the state of the joint. The joint inspection apparatus includes: a three-dimensional shape measuring device measuring joint features; a classifying device judging a state of a joint by at least two joint features transmitted by the three-dimensional shape measuring device; and a user interface device displaying the state of the joint, wherein the state of the joint is displayed in a joint space graph in which a user may easily adjust a judgment reference.

9 Claims, 9 Drawing Sheets

(56) References Cited

U.S. PATENT DOCUMENTS

| | | | |
|---|---|---|---|
| 2004/0049758 A1* | 3/2004 | Ueda et al. | 716/15 |
| 2004/0101190 A1* | 5/2004 | Maida et al. | 382/150 |
| 2004/0220770 A1* | 11/2004 | Isumi et al. | 702/179 |
| 2005/0102052 A1* | 5/2005 | Yoshida et al. | 700/117 |
| 2008/0040058 A1* | 2/2008 | Fujii et al. | 702/81 |
| 2009/0221103 A1* | 9/2009 | Watanabe | 438/14 |
| 2010/0007896 A1* | 1/2010 | Fishbaine | 356/603 |
| 2010/0034452 A1* | 2/2010 | Gines | 382/132 |
| 2012/0149136 A1* | 6/2012 | Watanabe | 438/15 |
| 2012/0218562 A1* | 8/2012 | Ogino et al. | 356/610 |
| 2012/0243771 A1* | 9/2012 | Matsumoto et al. | 382/141 |
| 2012/0294508 A1* | 11/2012 | Wada et al. | 382/150 |
| 2013/0089239 A1* | 4/2013 | Ikeda et al. | 382/106 |
| 2014/0133738 A1* | 5/2014 | Jeong | 382/150 |

* cited by examiner

FIG. 6

| JOINT HEIGHT | PAD HEIGHT | STEEP AREA RATIO | NON-FLAT AREA RATIO | JUDGMENT |
|---|---|---|---|---|
| 0 | 0 | 0 | 0 | BADNESS |
| 0 | 0 | 0 | 1 | BADNESS |
| ... | ... | ... | ... | ... |
| 0 | 0 | 1 | 1 | GOODNESS |
| 0 | 0 | 1 | 2 | GOODNESS |
| ... | ... | ... | ... | ... |
| 2 | 2 | 2 | 1 | BADNESS |
| 2 | 2 | 2 | 2 | BADNESS |

JOINT INSPECTION APPARATUS

CROSS REFERENCE TO RELATED APPLICATION

This application claims the benefit of Korean Patent Application No. 10-2012-0032152, filed on Mar. 29, 2012, entitled "Joint Inspection apparatus", which is hereby incorporated by reference in its entirety into this application.

BACKGROUND OF THE INVENTION

1. Technical Field

The present invention relates to a joint inspection apparatus, and more particularly, to a joint inspection apparatus for judging whether an electronic component mounted on a board is appropriately soldered to the board.

2. Description of the Related Art

Most of the electronic products include electronic components mounted on a printed circuit board (PCB) (hereinafter, referred to as a 'board'). Generally, electronic components such as a chip are electrically connected to the board using a solder. However, when the electronic components are not appropriately connected to a pad of the printed circuit board (hereinafter, referred to as a 'pad'), a problem such as contact badness, disconnection, or the like, occurs. Therefore, it is very important to confirm whether or not a terminal of the electronic components (hereinafter, referred to as a 'terminal') is normally connected to the pad through the pad.

According to the related art, in order to judge whether or not the terminal is normally connected to the pad, a volume of solder at a portion (hereinafter, referred to as a 'joint') at which the terminal and the pad are coupled to each other is measured using a three-dimensional shape measuring device and is then compared with a boundary value to judge whether or not the electronic component is normally connected to the board, that is, whether the joint is good or bad. However, since the volume of solder measured at the joint (hereinafter, referred to as a 'joint volume') is a value affected by several factors such as how accurately a position of the terminal is extracted, to which region the pad set, whether or not the electronic component is accurately positioned on the board according to CAD information, and the like, a method of judging whether the joint is good or bad only with the joint volume has low reliability.

In addition, since a process in which a user views the CAD information of the electronic component and optimizes a reference for judging whether or the joint is good or bad by trials and errors should be performed, a user interface is inconvenient.

SUMMARY OF THE INVENTION

An object of the present invention is to provide a joint inspection apparatus of extracting at least two joint features and judging a state of a joint from a combination of the extracted joint features so that the state of the join may be more accurately judged.

Another object of the present invention is to provide a joint inspection apparatus including a user interface allowing a user to intuitively and easily change a reference for judging whether a joint is good or bad by a combination of joint features.

According to an exemplary embodiment of the present invention, there is provided a joint inspection apparatus including: a three-dimensional shape measuring device measuring joint features; a classifying device judging a state of a joint by at least two joint features transmitted by the three-dimensional shape measuring device; and a user interface device displaying the state of the joint.

The at least two joint features may include the three-dimensional joint feature and the two-dimensional joint feature.

The state of the joint may be displayed in a joint feature space graph.

In the joint feature space graph, a second joint feature space graph may be included in divided regions of a first joint feature space graph.

BRIEF DESCRIPTION OF THE DRAWINGS

The above and other objects, features and advantages of the present invention will be more clearly understood from the following detailed description taken in conjunction with the accompanying drawings, in which:

FIG. 6 is a diagram showing a judgment rule table for judging a state of the joint;

FIG. 7 is a two-dimensional joint feature space graph; to

DESCRIPTION OF THE PREFERRED EMBODIMENTS

Hereinafter, a joint inspection apparatus according to an exemplary embodiment of the present invention will be described in more detail with reference to the accompanying drawings.

Figure 1:
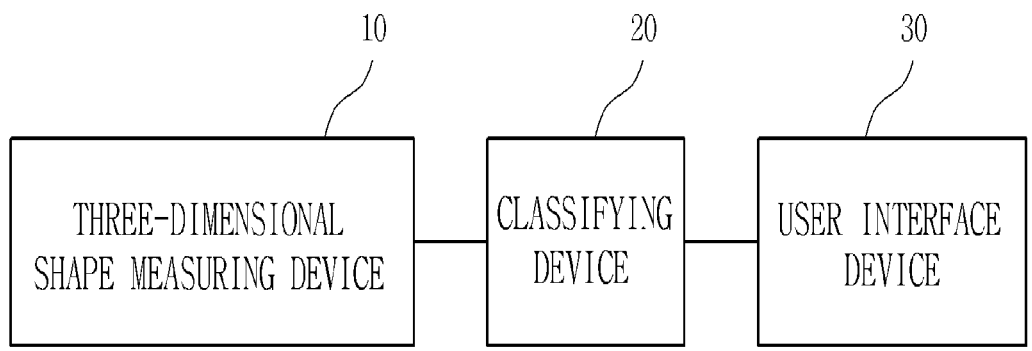
FIG. 1 is a block diagram showing a configuration of a joint inspection apparatus according to an exemplary embodiment of the present invention.

FIG. 1 is a block diagram showing a configuration of a joint inspection apparatus according to an exemplary embodiment of the present invention. The joint inspection apparatus according to the exemplary embodiment of the present invention is configured to include a three-dimensional shape measuring device 10, a classifying device 20, and a user interface device 30. The entire operation scheme of the joint inspection apparatus according to the exemplary embodiment of the present invention will be described below. When the three-dimensional shape measuring device 10 measures a plurality of joint features for an electronic component on a board, the classifying device 20 classifies states of joints according to boundary values set for each joint feature and the user interface device 30 displays the states of the joints using a joint feature space graph. A user may set and change the states of the joints displayed on the joint feature space graph and the boundary values for each joint feature using the user interface device 30. Hereinafter, the respective components will be described in detail.

Figure 2:
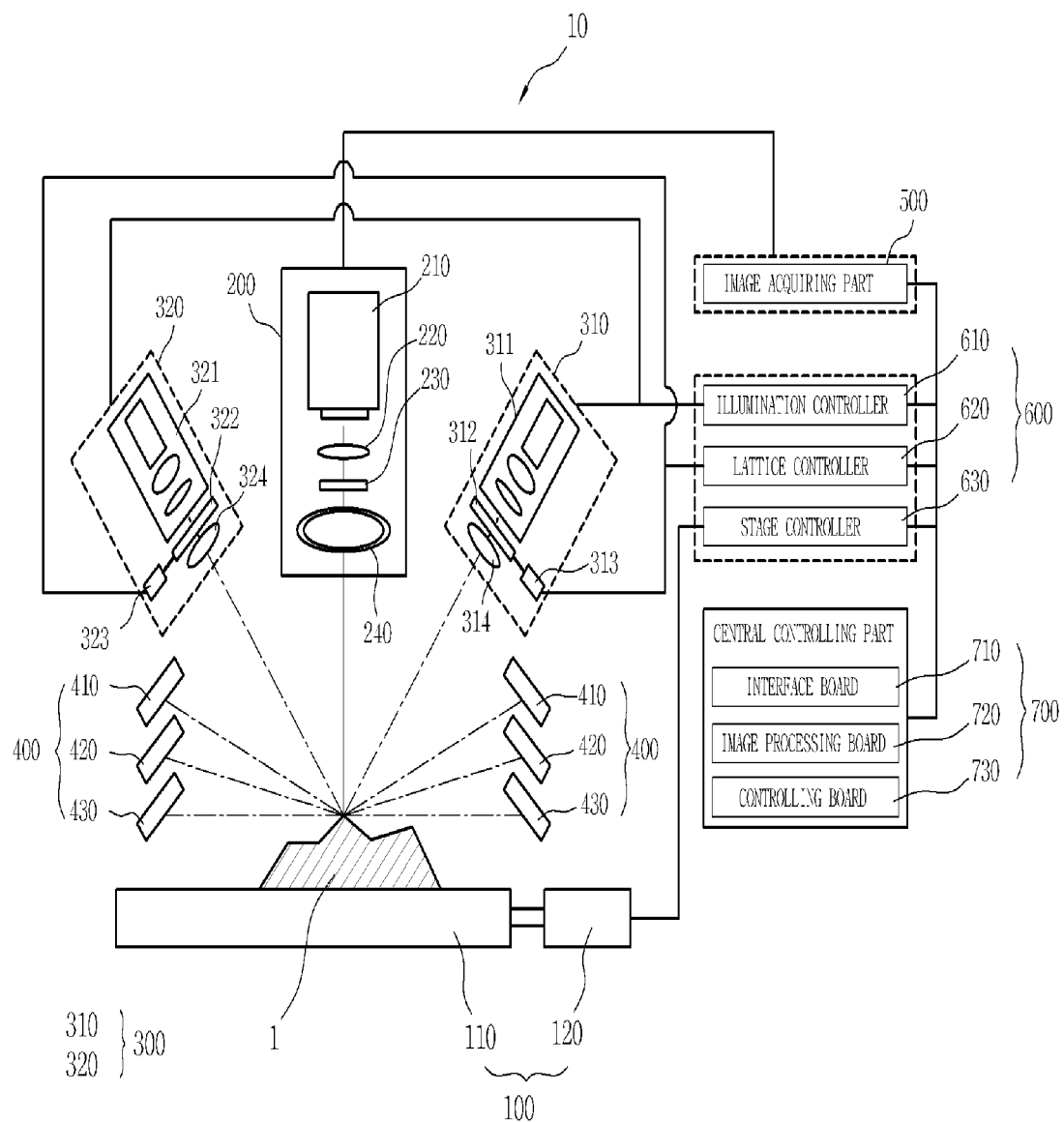
FIG. 2 is a diagram showing a three-dimensional shape measuring device according to the exemplary embodiment of the present invention.

FIG. 2 is a diagram showing a three-dimensional shape measuring device 10 according to the exemplary embodiment of the present invention.

The three-dimensional shape measuring device 10 includes a measuring stage part 100, an image photographing part 200, a first illuminating part 300, a second illuminating part 400, an image acquiring part 500, a module controlling part 600, and a central controlling part 700.

In detail, the measuring stage part 100 may include a stage 100 supporting an object 1 to be measured and a stage transferring unit 120 transferring the stage 110. As the object 1 to be measured moves with respect to the image photographing part 200, the first illuminating part 300, and the second illuminating part 400 by the stage 110, a measurement position of the object 1 to be measured may be changed.

The image photographing part 200, which is a component disposed over the stage 110 and measuring an image of the object 1 to be measured using light emitted from the first illuminating part 300 or the second illuminating part 400 and reflected from the object 1 to be measured as an input signal, may include a camera 210, an imaging lens 220, a filter 230, and a circular lamp 240. The camera 210 photographs the image of the object 1 to be measured using the light reflected from the object 1 to be measured as the input signal and may be, for example, any one of a charge coupled device (CCD) camera and a complementary metal oxide semiconductor (CMOS) camera. The imaging lens 220 is disposed under the camera 210 and images the light reflected from the object 1 to be measured in the camera 210. The filter 230 is disposed under the imaging lens 220 and filters the light reflected from the object 1 to be measured to provide the filtered light to the imaging lens and may be, for example, any one or a combination of at least two of a frequency filter, a color filter, and a light intensity adjusting filter. The circular lamp 240 may be disposed under the filter 230 and emit light to the object 1 to be measured in order to photograph a specific image such as a two-dimensional image of the object 1 to be measured.

The first illuminating part 300 may include a plurality of illuminating modules disposed at a side of the image photographing part 200 so as to be inclined with respect to the stage 110 supporting the object 1 to be measured. Hereinafter, the case in which the first illuminating part 300 includes two illuminating modules, that is, a first illuminating module 310 and a second illuminating module 320 as shown in FIG. 2 will be described.

The first illuminating module 310 includes a first illuminating unit 311, a first lattice unit 312, a first lattice transferring unit 313, and a first lens unit 314 and is disposed at one side of the image photographing part 200, for example, the right side of the image photographing part 200 so as to be inclined with respect to the stage supporting the object 1 to be measured. The first illuminating unit 311 is configured of an illuminating source and at least one lens to generate light, and the first lattice unit 312 is disposed in a direction in which the first illuminating unit 311 emits the light and changes the light generated in the first illuminating unit 311 into first lattice pattern light having a lattice pattern. The first lattice transferring unit 313 is coupled to the first lattice unit 312 to transfer the first lattice unit 312 and may be, for example, any one of a piezoelectric (PZT) transferring unit and a fine linear transferring unit. The first lens unit 314 is disposed in the direction in which the first lattice unit 312 emits the light and collects the first lattice pattern light emitted from the first lattice unit 312 on the object 1 to be measured.

The second illuminating module 320 may be disposed at the left side of the image photographing part 200 so as to be inclined with respect to the stage 110 supporting the object 1 to be measured and include a second illuminating unit 321, a second lattice unit 322, a second lattice unit 323, and a second lens unit 324. Since the second illuminating module 320 has the same configuration as that of the first illuminating module 310 described above, an overlapped detailed description will be omitted.

N first lattice pattern lights are irradiated on the object 1 to be measured with while the first lattice transferring unit 313 of the first illuminating module 310 sequentially moves the first lattice unit 312 N times, and the image photographing part 200 sequentially receives the N first lattice pattern lights reflected from the object 1 to be measured to photograph N first pattern images. Likewise, N second lattice pattern lights are irradiated on the object 1 to be measured with while the second lattice transferring unit 323 of the second illuminating module 320 sequentially moves the second lattice unit 322 N times, and the image photographing part 200 sequentially receives the N second lattice pattern lights reflected from the object 1 to be measured to photograph N second pattern images. Here, N, which indicates a natural number, may be for example, 3 or 4. The photographed N first pattern images and N second pattern images provide information on a height of the object 1 to be measured, that is, a three-dimensional joint feature through subsequent phase analysis. Since a detailed method of measuring the three-dimensional joint feature has been disclosed in Korean Patent No. 1059697 granted to the present applicant, a detailed description thereof will be omitted.

Although the case in which two illuminating modules 310 and 320 are used as the illuminating devices generating the lattice pattern lights has been described in the present embodiment, the number of illuminating modules may also be three or more. In addition, when the lattice pattern lights are irradiated on the object 1 to be measured in various directions, various kinds of pattern images may be photographed. For example, in the case in which three illuminating modules are disposed in a regular triangular shape based on the image photographing part 200, three lattice pattern lights may be irradiated on the object 1 to be measured in different directions, and in the case in which four illuminating modules are disposed in a square shape based on the image photographing part 200, fourth lattice pattern lights may be irradiated on the object 1 to be measured in different directions. Generally, the first illuminating part 300 may include any number of illuminating modules. In this case, any number of illuminating modules may be disposed on a circumference based on the image photographing part 200 and the lattice pattern lights may be irradiated to photograph pattern images.

The second illuminating part 400, which is a component irradiating light for acquiring a two-dimensional image of the object 1 to be measured to the object 1 to be measured, may include a first light source module 410, a second light source module 420, and a third light source module 430. The first light source module 410, the second light source module 420, and the third light source module 430 may include red, green, and blue light sources, respectively, be disposed in a circular shape over the object 1 to be measured, and irradiate each of red light, green light, and blue light to the object 1 to be measured. In addition, the respective light sources may be disposed at different heights to make incident angles of the lights irradiated to the object 1 to be measured different from each other, as shown in FIG. 2. Since angles at which the lights are irradiated to the object 1 to be measured are different from each other according to positions of the light source modules, images photographed by the lights emitted from the second illuminating part 400 are color images displayed by different colors according to an inclination of the object 1 to be measured and provides information on a two-dimensional joint feature. Since a detailed method of measuring the two-dimensional joint feature has been disclosed in Korean Patent No. 1059697 granted to the present applicant, a detailed description thereof will be omitted.

The image acquiring part 500, which is a component capable of transmitting or receiving data to or from the image photographing part 200, acquires and stores the pattern images associated with the three-dimensional joint feature and the color image associated with the two-dimensional feature that are photographed by the image photographing part 200.

The module controlling part 600, which is a component controlling the measuring stage unit 100, the image photographing unit 200, and the first illumination unit 300, includes an illumination controller 610, a lattice controller 620, and a stage controller 630. The illumination controller 610 controls each of the first and second illumination modules 310 and 320 to generate the lights, and the lattice controller 620 controls each of the first and second lattice transferring units 313 and 323 to move the first and second lattice units 312 and 322. The stage controller 630 may control the stage transferring unit 120 to vertically and horizontally move the stage 110.

The central controlling part 700, which is a component controlling the image acquiring part 500 and the module controlling part 600, may receive image data from the image acquiring part 500 to extract the two-dimensional joint feature and the three-dimensional joint feature of the object 1 to be measured. In addition, the central controlling part 700 may control each of the illumination controller 610, the lattice controller 620, and the stage controller 630 of the module controlling part 600. The central controlling part 700 may include an interface board 710, an image processing board 720, and a controlling board 730, transmits or receives control signals, image data, and the like, to or from the image acquiring part 500 and the module controlling part 600 through the interface board 710, processes the image data received from the image acquiring part 500 through the image processing board 720 to extract the two-dimensional joint feature and the three-dimensional joint feature, and generally controls the three-dimensional shape measuring device 10 through the controlling board 730.

Figure 3:
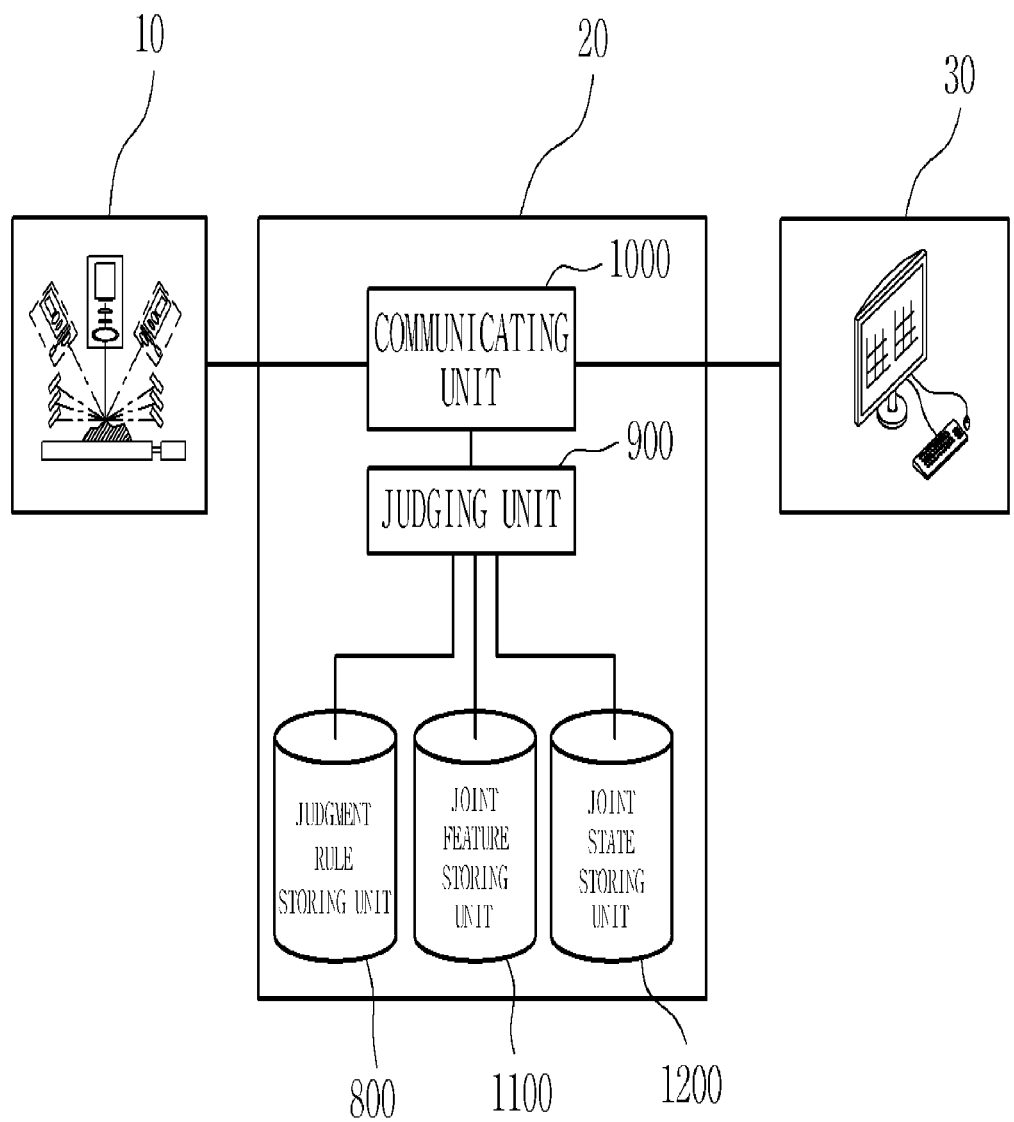
FIG. 3 is a diagram showing a classifying device according to the exemplary embodiment of the present invention.

FIG. 3 is a diagram showing a classifying device 20 according to the exemplary embodiment of the present invention.

The classifying device 20 may include a judgment rule storing unit 800 storing a judgment rule for judging a state of a joint by a joint feature measured by the three-dimensional shape measuring device 10, a judging unit 900 comparing the joint feature measured by the three-dimensional shape measuring device 10 with the judgment rule stored in the judgment rule storing unit 800 to judge the state of the joint, and a communicating unit 1000 transmitting and receiving data between the classifying device 20 and the third-dimensional shape measuring device 10 and between the classifying device 20 and the user interface 30. In addition, the classifying device 20 may further include a joint feature storing unit 1100 storing the joint feature measured by the three-dimensional shape measuring device 10 and a joint state storing unit 1200 storing joint state data including data on whether or not the measured joint is good or bad.

More specifically, the judgment rule storing unit 800 is a component storing the judgment rule for judging the state of the joint, wherein the judgment rule may be stored in a form of a table (hereinafter, referred to as a 'judgment rule table'). An example of a judgment rule table having a simple form may include a judge rule table in which the number of joint features associated with judgment is two and one boundary value is set for each joint feature, such that it is judged that the state of the joint is good when each joint feature is the boundary value or more and it is judged that the state of the joint is bad when each joint feature is less the boundary value. In this case, since the state of the joint is classified only into goodness or badness, the judgment rule becomes simple. However, a problem is generated in processing the case in which it is unclear that it is certainly judged that the state of the joint is good or bad.

The above-mentioned problem may be solved by increasing the number of boundary values for each joint feature. For example, in the case in which the number of joint features is two and two boundary values are set for each joint feature, a feature region may be classified into three regions such as goodness, judgment impossibility, and badness for each joint. Therefore, with the joint feature classified into the judgment impossibility since it may not be certainly judged that the state of the joint is good or bad, the joint feature is again measured or a person directly tests the state of the joint, thereby making it possible to certainly classify the state of the joint.

When this is extended to a general case, in the case in which the number of features is n and a boundary value of a k-th joint feature is $m_k$, the judgment rule table may define the state of the joint with respect to the number of $(m_1+1) \times (m_2+1) \times (m_3+1) \times \ldots \times (m_n+1)$ cases.

The judging unit 900 is a component comparing the joint feature with the judgment rule stored in the judgment rule storing unit 800 to judge the state of the joint. A judgment result of the judging unit 900 is generated as joint state data. For example, a judgment result for four joint features may be generated as set data such as {goodness, goodness, judgment impossibility, goodness}. According to the related art, since it may be appreciated only whether the state of the joint is good or bad, it was difficult to find a cause of the badness. However, according to the exemplary embodiment of the present invention in which it may be appreciated whether each joint feature is good or bad, in the case in which the joint is bad, the cause of the badness may be more easily found. For example, when a ratio in which a judgment result of a steep area ratio, which is one of the joint features, becomes the judgment impossibility or the badness is high in any printed circuit board, since it means that a solder is not formed at an appropriate angle between a terminal and a pad, it may be easily appreciated that a problem is present in a soldering process.

The communicating unit 1000 may receive the judgment result from the judging unit 900 to transmit the received judgment result to a user interface device 30 to be described below, receive the judgment rule set or changed through the user interface device 30 by the user to transmit the received judgment rule to the judgment rule storing unit 800, and receive the joint state data set or changed through the interface device 30 by the user to transmit the joint state data to the joint state storing unit 1200.

The joint feature storing unit 1100 stores the joint features and provides the stored joint features to the judging unit 900 when the stored joint features are requested by the judging unit 900. In this case, after all of the measurable joint features are stored, only several features required by the judging unit 900 may be transmitted.

The joint state storing unit 1200 stores the joint state data. The joint state data may be joint state data generated according to the judgment result of the judging unit 900 or joint state data set by the user and be subsequently changed through the user interface device 30 by the user.

Figure 4:
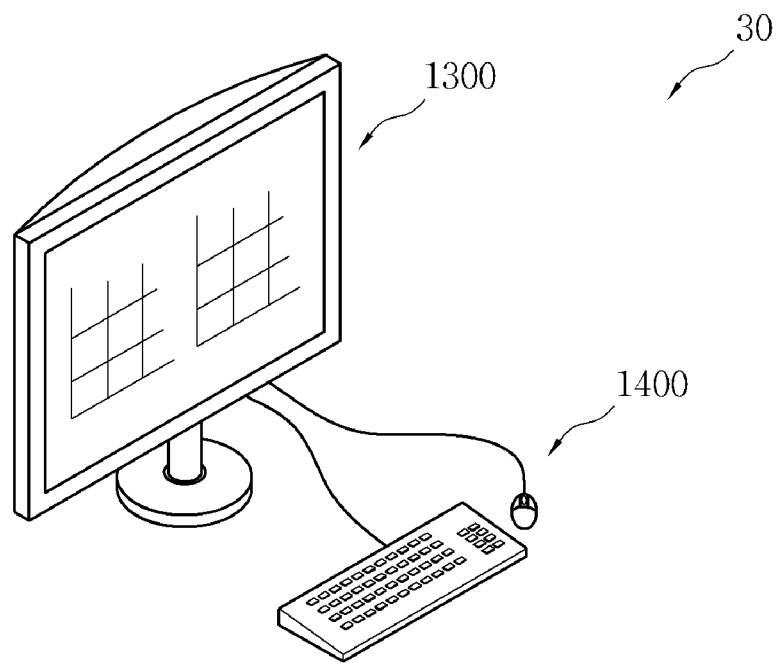
FIG. 4 is a diagram showing a user interface device according to the exemplary embodiment of the present invention.

FIG. 4 is a diagram showing a user interface device 30 according to the exemplary embodiment of the present invention.

The user interface device 30 may include a display unit 1300 and an input unit 1400.

More specifically, the display unit 1300, which is a component allowing the joint features to be viewed on a single screen, displays a joint feature space graph and joints in the joint feature space graph. In addition, since boundary values are set in a joint feature space, to which region the joints belong based on the boundary values for each feature may be recognized.

The input unit 1400 is a component allowing a user to set or change the joint feature space, the boundary value for each joint feature, the joint state data, and the like, through the screen displayed on the display unit 1300. In the joint inspection apparatus according to the exemplary embodiment of the present invention, a general keyboard and a mouse are used as the input unit 1400.

In addition, the user interface device 30 may be provided in a touch screen form in which the display unit and the input unit are formed integrally with each other.

Hereinabove, the joint inspection apparatus according to the exemplary embodiment of the present invention has been described. The joint inspection apparatus according to the exemplary embodiment of the present invention may be generally used in the case in which n joint features and $m_k$ (k=1, 2, 3, . . . , n) boundary values are present as described above. However, hereinafter, the case in which the number of joint features is four (a joint height, a pad height, a steep area ratio, and a non-flat area ratio) and two boundary values are present for each joint feature, such that the joint features are classified into goodness, judgment impossibility, and badness will be described for convenience of explanation.

First, the joint feature is selected. The joint feature may be mainly classified into a 3D feature including height information and a 2D feature including color information. Although the 3D feature is selected as the joint height (JH) and the pad height (PH) and the 2D feature is selected as the steep area ratio (SAR) and the non-flat area ratio (NFAR) in the present embodiment, the joint feature may be appropriately defined and used according to a characteristic of an object to be measured to which the joint inspection apparatus according to the exemplary embodiment of the present invention is applied. In addition, the number of joint features that may be selected is not limited.

Figure 5:
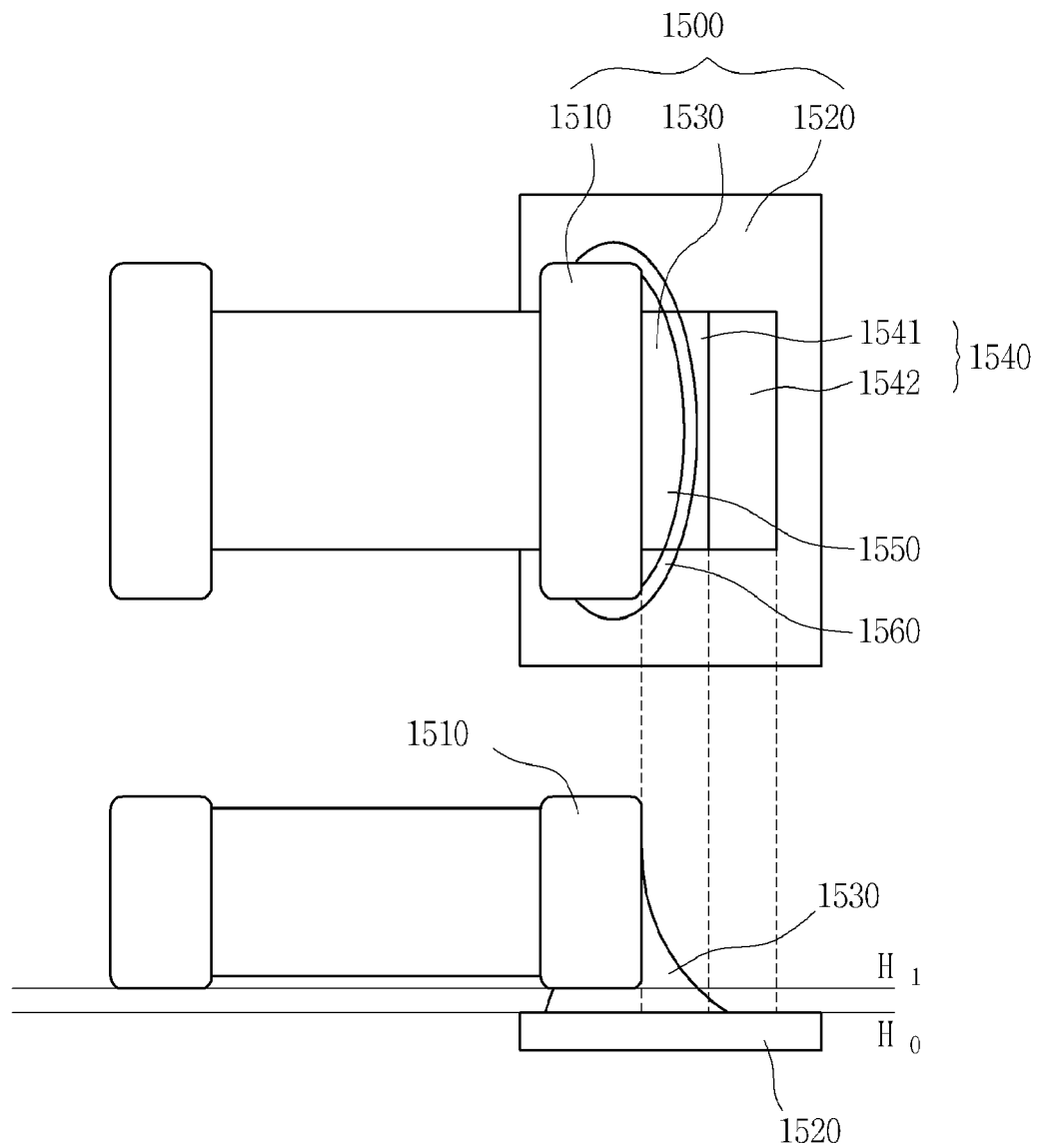
FIG. 5 is a plan view and a front view of a joint shown in order to define a joint feature.

FIG. 5 is a plan view and a front view of a joint 1500 shown in order to define a joint feature in the present embodiment. In the plan view of the joint 1500, a terminal 1510 is positioned over a pad 1520, a solder 1530 is disposed on the pad 1520, and an inspection region 1540 for inspecting the joint 1500 is a rectangle present in the pad 1520 while having one side contacting an end of the terminal 1510. The inspection region 1540 is again divided into two sub-inspection regions. Here, in the divided inspection region 1540, a sub-inspection region near to the terminal is defined as a near inspection region 1541, and a sub-inspection region far from the terminal is defined as a far inspection region 1542. In addition, a region in which an angle formed by a surface of the solder 1530 and the pad is a predetermined angle (for example, 30 degrees) or more is defined as a steep region 1550, and a region disposed at an outer side of the steep region and having the solder is defined as a saturated region 1560.

The joint height (JH) means an average height of the near inspection region 1541 and is defined as an average value of values normalized by dividing height values of the respective pixels in the near inspection region 1541 by a height value of the terminal 1510. Here, a measurement starting point of the height values of the respective pixels in the near inspection region 1541 is a height ($H_1$ in FIG. 5) at which a bottom of the terminal 1510 is positioned, and the height at which the bottom of the terminal is positioned may be calculated by subtracting a thickness of the terminal defined on CAD from the measured height value of the terminal. An advantage that may be achieved by setting the measurement starting point to the height at which the bottom of the terminal is positioned rather than a pad surface is that the joint height is less affected by accuracy of arrangement of the pad surface and the height is measured to be 0 in the case in which the joint is not formed between the terminal and the pad as in cold soldering, such that badness may be easily detected.

The pad height (PH) means an average height in the far inspection region 1542 and is defined as an average value of values normalized by dividing height values of the respective pixels in the far inspection region 1542 by the height value of the terminal. A measurement starting point of the pad height (PH) is the pad surface ($H_0$ in FIG. 6). In the case of the cold soldering, the pad is easily formed in the far inspection region 1542, in the case in which the pad height is measured to be high, badness may be easily detected.

The steep area ratio (SAR) means a ratio in which the solder 1530 is formed at a predetermined steep angle or more in the near inspection region 1541 and is defined as a value obtained by dividing an area of a region in which the solder 1530 is formed at a predetermined angle or more based on the pad surface by an area of the near inspection region 1541. Here, the region in which the solder 1530 is formed at the predetermined angle or more may be recognized by reading an image obtained by photographing the lights emitted from the first light source module 410, the second light source module 420, and the third light source module 430 disposed to have different incident angles in the second illuminating part 400 of the three-dimensional shape measuring device 10 according to the exemplary embodiment of the present invention.

The non-flat area ratio (NFAR) means a ratio of a non-flat region in the inspection region 1520 and is defined as a value obtained by dividing an area obtained by summing up the steep region 1550 and the saturated region 1560 in the vicinity of the steep region by the entire area of the inspection region 1540.

When the four joint features defined in the present embodiment are measured, the judging unit 900 judges the state of the joint for each joint feature. In this case, the judging unit 900 may collectively receive only joint features required for judging the state of the joint among the joint features stored in the joint feature storing unit 1100.

FIG. 6 is a diagram showing an example of a judgment rule table for judging a state of the joint according to the present embodiment. Since two boundary values are assumed for each joint feature in the present embodiment, a joint feature space is divided into three sections, and the sections divided from the joint feature space are denoted by 0, 1, and 2 in a sequence in which values are low. For example, the joint height of 0 means that the joint height is low, the joint height of 1 means that the joint height is medium, and the joint height of 2 means that the joint height is high.

That is, in the case in which the joint height is low (JH=0), the pad height is low (PH=0), the steep area rate is medium (SAR=1), and the non-flat area ratio is medium or large (NFAR=1 or 2) in the judgment rule table of FIG. 6, it is judged that a corresponding joint is good.

The judging unit 900 compares the joint feature with the judgment rule stored in the judgment rule storing unit 800 to judge the state of the joint for each joint feature and transmits the joint state data to the joint state storing unit 1200.

Next, the user interface device 30 displaying the state of the joint and allowing the user to adjust the boundary value for each joint feature in the joint inspection apparatus according to the exemplary embodiment of the present invention will be described.

Figure 7:
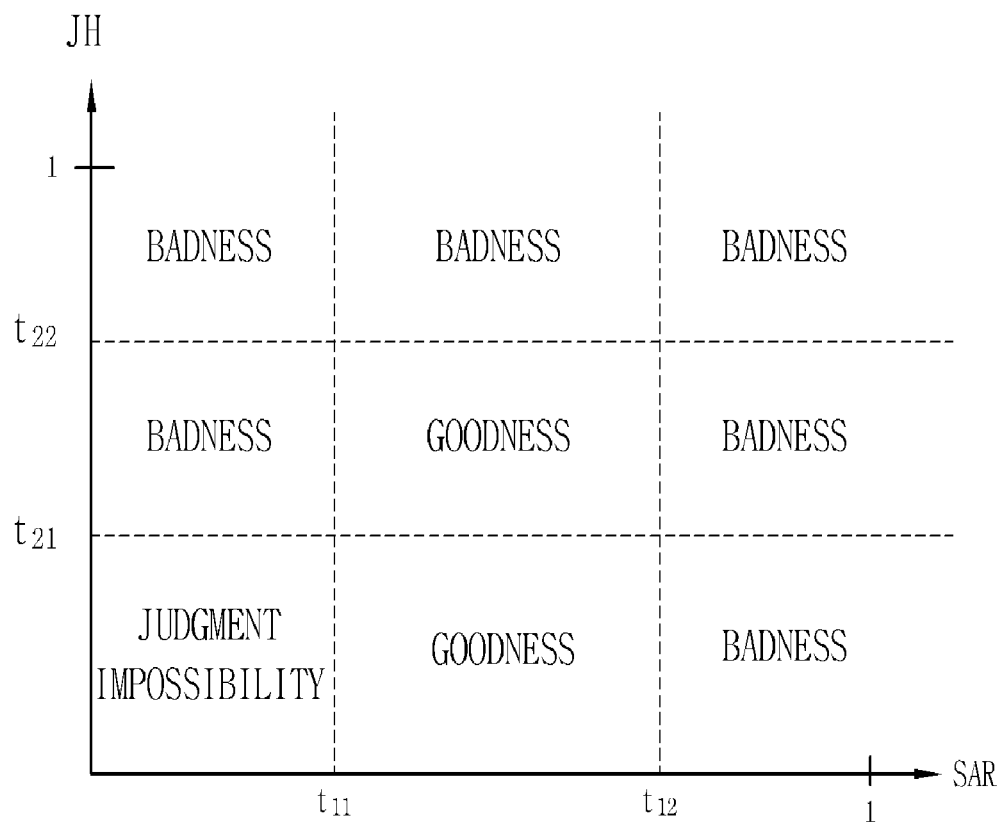

For example, when the number of joint features is two, the state of the joint may be intuitively represented by a two-dimensional graph regardless of the number of boundary values for each joint feature. FIG. 7 is a view showing an example of a two-dimensional joint feature space graph displayed on the user interface device 30 according to the exemplary embodiment of the present invention. This graph is a joint feature space graph in the case in which joint features are a steep area ratio (SAR) and a joint height (JH), boundary values of the steep area ratio are $t_{11}$ and $t_{12}$, and boundary values of the joint height are $t_{21}$ and $t_{22}$.

In FIG. 7, in the case in which the steep area ratio is equal to or larger than $t_{11}$ and less than $t_{12}$, that is, medium, and the joint height is less than $t_{22}$, that is, low or medium, it is judged that the state of the joint is good, in the case in which the steep area ratio is less than $t_{11}$ and the joint height is less than $t_{21}$, that is, both of the joint height and the steep area ratio are low, the state of the joint may not be judged, and in other cases, it is judged that the state of the joint is bad.

With the user interface as described above, since the state of the joint may be recognized when it is recognized whether a space to which the joint belongs is good, may not be judged, or bad, the user may intuitively and simply judge the state of the joint. In addition, the reference for judging the state of the joint may be easily changed by moving the boundary value in a scheme of clicking and then dragging the boundary value using a mouse in the user interface device 30, or the like.

When the number of joint features is two as in the case of FIG. 7, the joints may be represented on the two-dimensional joint feature space graph. However, when the number of joint features is three or more, particularly, when the number of joint features is four or more, it is difficult to provide an intuitive interface to the user.

Figure 8:
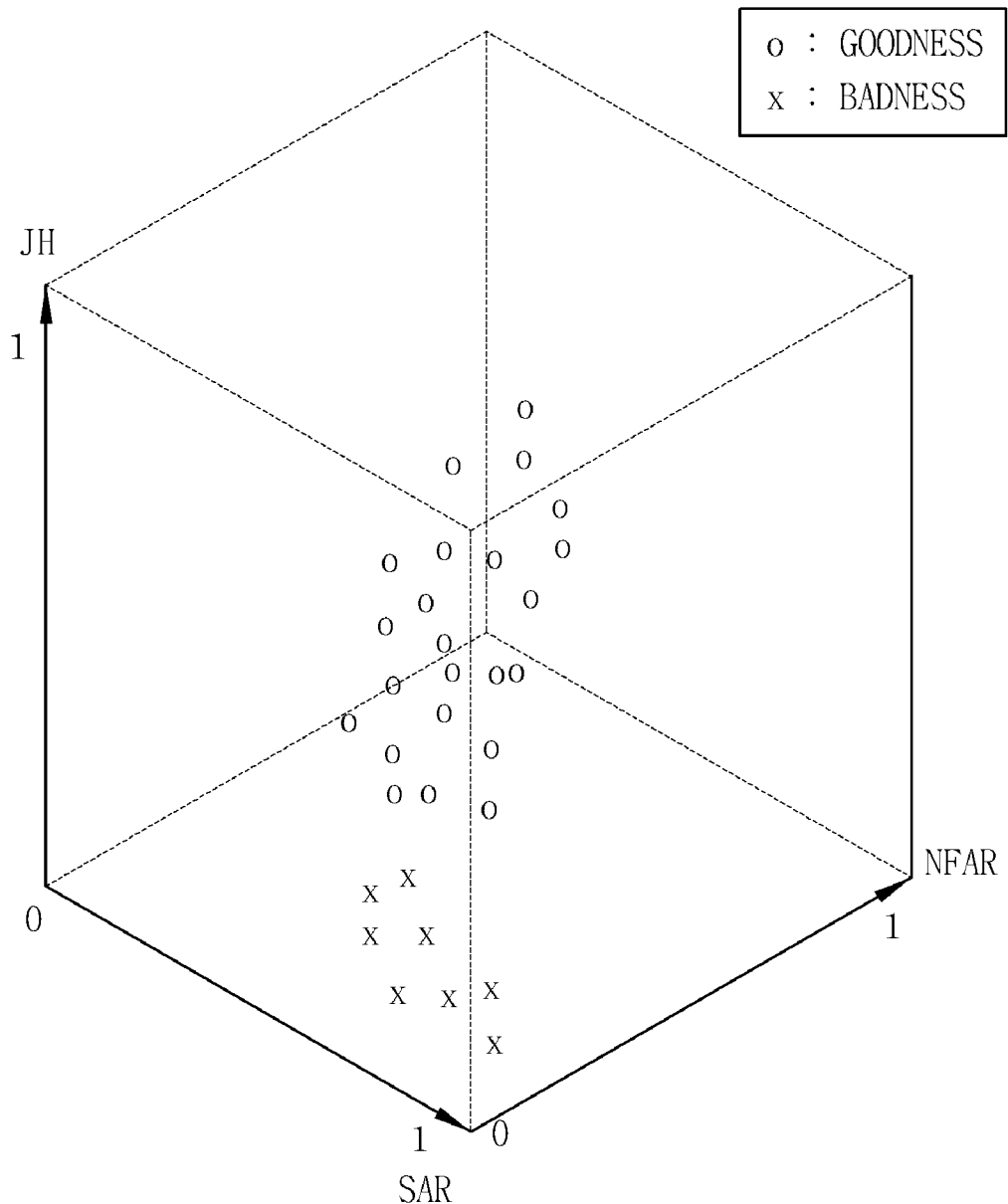
FIG. 8 is a three-dimensional joint feature space graph.

First, the case in which the number of joint features is three will be described. As shown in FIG. 8, a three-dimensional joint feature space graph and joints are displayed on the user interface 30, thereby making it possible to allow the user to judge the state of the joint and change the boundary value.

However, in the case in which the number of joint features is four or more, since four or more dimensions are simultaneously displayed on the graph, there is a problem that it is difficult to implement four or more dimensions in a general display device. According to the exemplary embodiment of the present invention, in order to solve the above-mentioned problem, the joint feature space graph is implemented by dividing a joint feature space and allowing a sub joint feature space to correspond to the divided joint feature space.

A detailed method thereof will be described below. When there are four joint features, a two-dimensional joint feature space is first formed by two joint features. Then, a joint feature space is formed by two joint features other than the above-mentioned two joint features in a region divided by a boundary value in the two-dimensional joint feature space.

Figure 9:
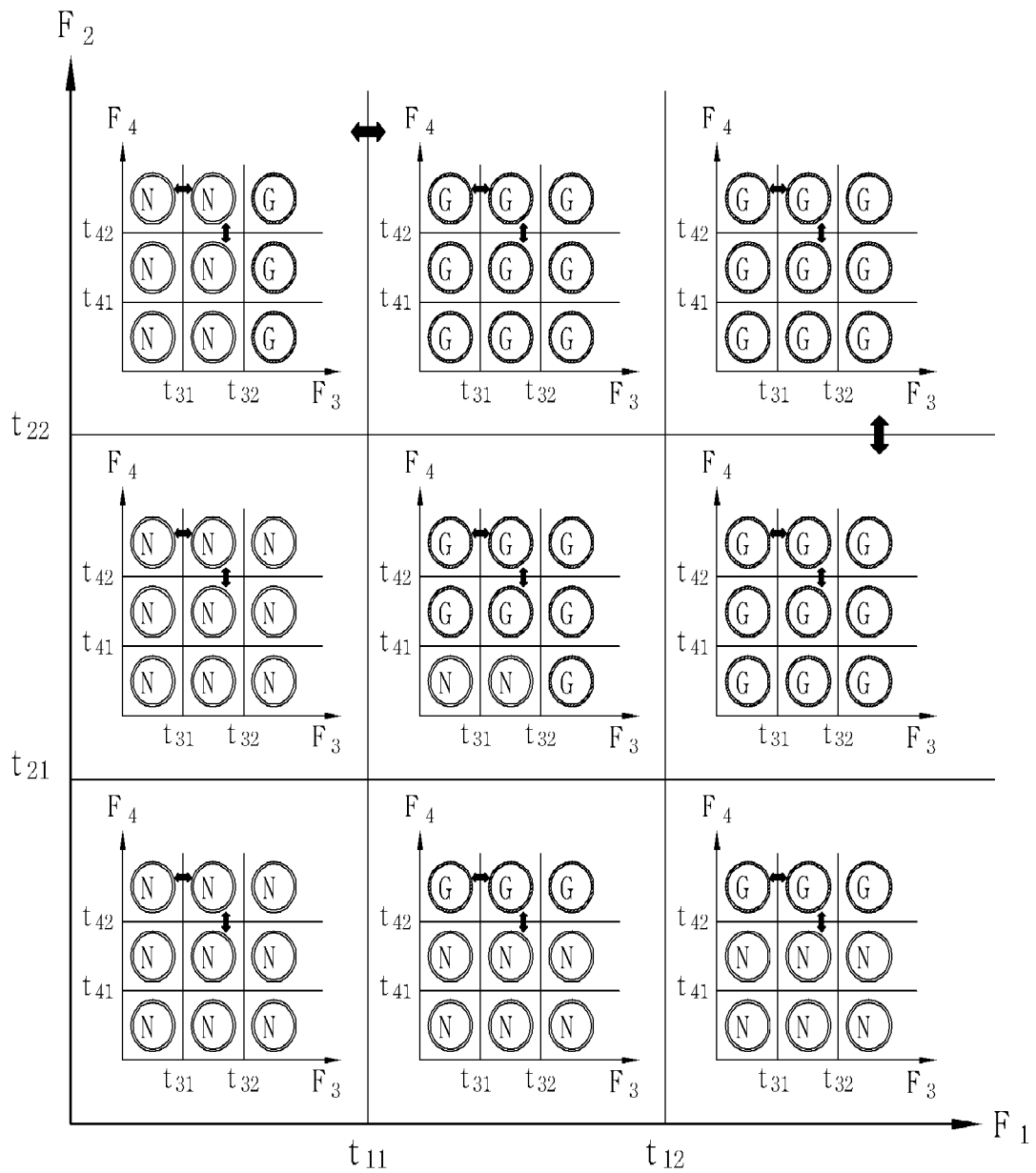
FIG. 9 is a four-dimensional joint feature space graph.

FIG. 9 is a diagram showing a four-dimensional joint feature space graph in the case in which there are four joint features (G indicates goodness and NG indicates badness).

Since the joint features may be arbitrarily combined with each other, when it is assumed that four joint features are $F_1$, $F_2$, $F_3$, and $F_4$, respectively, a first joint feature space is first formed by $F_1$ and $F_2$. In this case, the joint features forming the first joint feature space or a second joint feature space may be configured of a combination of a three-dimensional joint feature and a two-dimensional joint feature. Nine divided regions are formed by boundary values $t_{11}$, $t_{12}$, $t_{21}$, and $t_{22}$ in the first joint feature space, and the second feature space formed by $F_3$ and $F_4$ is represented in each of the nine divided regions. Each of the second joint feature spaces is again divided into nine regions by boundary values $t_{31}$, $t_{32}$, $t_{41}$, and $t_{42}$, and the joint feature $F_1$, $F_2$, $F_3$, and $F_4$ are represented in each of the divided regions of the second joint feature space. That is, since the joint state in the joint feature space may be recognized in a single screen even though there are four joint features, the user may intuitively and simply judge the state of the joint. With the method as described above, it will be obvious to those skilled in the art that in the case in which there are n joint features, a joint feature space graph may be shown.

In addition, the user may easily change the boundary values in the joint feature space graph displayed on the user interface device 30. For example, when $t_{42}$ is moved in a vertical direction, since all $t_{42}$ values are changed together in the nine sub joint feature spaces formed by $F_3$ and $F_4$, a joint feature judgment reference by $F_4$ may be easily changed.

In addition, the user specifies (clicks the left or the right of the mouse) the joint represented in the joint feature space graph displayed on the user interface device 30, thereby making it possible to change the state of the joint. This may be utilized to set the boundary value for judging the state of the joint. For example, in the case in which it is judged that the state of the joint is good even though it is obvious that the state of the joint is bad, since a judgment reference is erroneously set, the user specifies a corresponding joint judged to be good to change the state of the corresponding joint into a bad state and change the boundary value so that the corresponding joint belongs to the bad states, thereby making it possible to allow an error not to be generated in subsequently judging the state of the joint. In this case, the changed state of the joint is stored in the joint state storing unit 1200, and the changed boundary value is stored in the judgment rule storing unit 800.

The joint inspection apparatus according to the exemplary embodiment of the present invention judges the state of the joint in consideration of a plurality of joint features, thereby making it possible to increase accuracy of judgment.

In addition, the user may easily set and change the state of the joint and the judgment reference through an intuitive user interface.

What is claimed is:

1. A joint inspection apparatus comprising:
   a three-dimensional shape measuring device measuring joint features of a joint;
   a classifying device judging a state of the joint by at least two joint features transmitted by the three-dimensional shape measuring device, the at least two joint features including a two-dimensional joint feature which is a steep area ratio or a non-flat area ratio; and
   a user interface device displaying the state of the joint.

2. The joint inspection apparatus of claim 1, wherein the three-dimensional shape measuring device measures a three-dimensional joint feature and the two-dimensional joint feature of the joint.

3. The joint inspection apparatus of claim 2, wherein the three-dimensional joint feature is a joint height or a pad height.

4. The joint inspection apparatus of claim 1, wherein the state of the joint is displayed in a joint feature space graph.

5. The joint inspection apparatus of claim 4, wherein in the joint feature space graph, a second joint feature space graph is included in divided regions of a first joint feature space graph.

6. The joint inspection apparatus of claim 5, wherein joint features forming the first joint feature space or the second joint feature space are configured of a combination of the three-dimensional joint feature and the two-dimensional joint feature.

7. The joint inspection apparatus of claim 1, wherein the classifying device includes:
   a judgment rule storing unit storing a judgment rule for judging the state of the joint by the joint feature measured by the three-dimensional shape measuring device;
   a judging unit comparing the joint feature measured by the three-dimensional shape measuring device with the judgment rule stored in the judgment rule storing unit to judge the state of the joint; and
   a communicating unit transmitting and receiving data between the classifying device and the third-dimensional shape measuring device and between the classifying device and the user interface.

8. The joint inspection apparatus of claim 7, wherein the classifying device further includes:
   a joint feature storing unit storing the joint feature measured by the three-dimensional shape measuring device; and
   a joint state storing unit storing the state of the joint.

9. The joint inspection apparatus of claim 1, wherein the user interface device includes:
   a display unit displaying a joint feature space graph and joints in the joint feature space graph; and
   an input unit setting or changing a joint feature space, a boundary value for each joint feature, and joint state data on a screen displayed on the display unit.

* * * * *